United States Patent [19]
Enström

[11] Patent Number: 5,421,347
[45] Date of Patent: Jun. 6, 1995

[54] DISPOSABLE LANCET DEVICE FOR PUNCTURING SKIN

[76] Inventor: Hans Enström, Box 7013, S-151 07, Södertälje, Sweden

[21] Appl. No.: 137,027
[22] PCT Filed: May 5, 1992
[86] PCT No.: PCT/SE92/00288
  § 371 Date: Oct. 18, 1993
  § 102(e) Date: Oct. 18, 1993
[87] PCT Pub. No.: WO92/19164
  PCT Pub. Date: Nov. 12, 1992

[30] Foreign Application Priority Data
May 7, 1991 [SE] Sweden ............................ 9101376

[51] Int. Cl.⁶ ............................................ A61B 17/34
[52] U.S. Cl. .................................. 128/754; 123/751; 123/749
[58] Field of Search ............... 128/749, 751, 754, 759; 606/167, 171, 181, 182, 172

[56] References Cited

U.S. PATENT DOCUMENTS

| | | |
|---|---|---|
| 2,442,416 | 6/1948 | Kulicke, Jr. |
| 4,320,769 | 3/1982 | Eichhorn et al. |
| 4,553,541 | 11/1985 | Burns |
| 4,616,649 | 10/1986 | Burns |
| 4,624,253 | 11/1986 | Burns |
| 4,676,244 | 6/1987 | Enstrom |
| 4,677,979 | 7/1987 | Burns ............... 606/181 X |
| 4,712,548 | 12/1987 | Enstrom |
| 4,738,261 | 4/1988 | Enstrom |
| 4,889,117 | 12/1989 | Stevens |
| 5,304,192 | 4/1994 | Crouse ............... 606/181 |

FOREIGN PATENT DOCUMENTS 2074453  11/1981  United Kingdom ............... 606/181

*Primary Examiner*—Sam Rimell
*Attorney, Agent, or Firm*—Nixon & Vanderhye

[57] ABSTRACT

A device for obtaining blood comprising a rod (1) with a lancet (5), a sleeve (2), a stop (9, 15) which temporarily prevents insertion of the rod into the sleeve in a starting position in which the lancet is located in the sleeve, and two spring tongues (16, 17) which abut against the rod so that the lancet is centred and retracted into the sleeve with the aid of the spring force in the tongues. According to the invention the tongues are defined by axial slits (23) in the wall of the sleeve, whereby the tongues extend obliquely into the sleeve with their ends (19) located inside the front end (14) or an orifice ring of the sleeve. The distance between the ends of the tongues when the rod assumes said starting position, is less than the thickness of the rod at the lancet end, and the tongues are arranged to cooperate with the lancet end upon movement of the lancet.

18 Claims, 2 Drawing Sheets

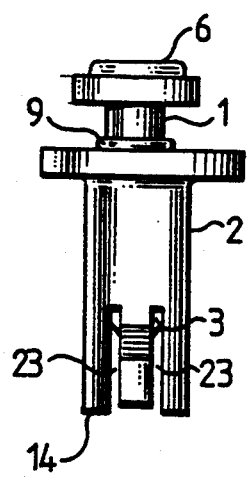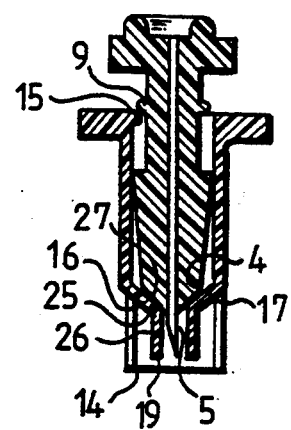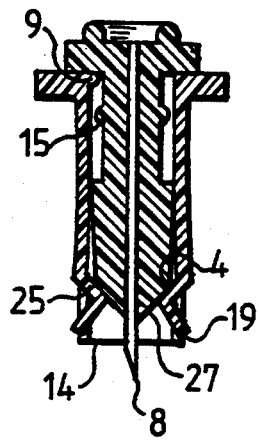

DISPOSABLE LANCET DEVICE FOR PUNCTURING SKIN

The present invention relates to a disposable device for puncturing skin and the blood vessels beneath to obtain blood for subsequent testing, said device comprising a rod with an elongate body and a lancet embedded therein with an axially protruding tip; a sleeve with a through-hole to receive the body of the rod via the rear end of the sleeve; first stop means formed by a first radial projection means arranged on the body of the rod at a predetermined distance from the tip of the lancet, in cooperation with a second radial projection means arranged on the sleeve at a predetermined distance from its front end, said first stop means temporarily preventing insertion of the rod and retaining the tip of the lancet inside the sleeve in a starting position located a predetermined distance from the front end of the sleeve, the arresting function of the first stop means being overcome by the application of external pressure on the rear end of the rod; a second stop means formed by a pressure plate at the rear end of the rod, in cooperation with the rear end of the sleeve, said second stop means determining the operative end position of the tip of the lancet when it protrudes from the sleeve; and at least two longitudinal spring tongues made in one piece with the sleeve, distributed uniformly around its periphery, and extending into the sleeve to abut against the body of the rod thereby centering it and the lancet being retracted into the sleeve with the aid of the spring force produced in the tongues when the rod is pressed into the sleeve with the aid of said external force.

A device of the type described in the introduction is known through SE-8003057-0. Essential advantages with this type of device are that the rod and sleeve can be manufactured together in a single tool, the preferably needle-shaped lancet being embedded in the device so that it is fixed in the rod, its tip portion is enclosed in the sleeve and is therefore sterile, and it can easily be twisted to remove it from the sleeve when it is to be used. A finished sterile device can thus be obtained at a single injection moulding procedure and the device can therefore be manufactured at low cost. Although the known device gives a relatively low and brief sensation of pain when the lancet penetrates the skin, which occurs extremely quickly thanks to its special design, however, certain people may experience a somewhat higher sensation of pain than normal. In many cases this may be because the rod is not kept centred in the sleeve, the tip of the lancet being able to move freely outwards in any radial direction during the forward movement of the rod. This off-centering is caused by the necessity of a gap between rod and sleeve. Said oblique displacement of the lancet is particularly likely to occur if the external pressure is applied with a finger slithtly to the side of the pressure plate of the rod instead of centrally. Another drawback with the known device is that the lancet remains outside the sleeve after use, the remaining blood thereby constituting a serious infection risk. U.S. Pat. No. 4,616,649 and U.S. Pat. No. 4,624,253 describe different arrangements for solving the two problems just mentioned individually, but this is at the expense of poorer main function of the device and more expensive and complicated manufacture. U.S. Pat. No. 4,553,541 describes a lancet device with spring tongues intended to return the lancet to a protected position. However, the tongues work against the movement of the lancet out of the sleeve and therefore have a retarding effect on the projection of the lancet. Furthermore, the device is designed in accordance with a completely different, more complicated principle than that according to the invention and cannot be produced in a single tool.

The object of the present invention is to provide an improved device which has spring tongues arranged so that they both centre the lancet during its rapid movement towards and through the skin in relation to the sleeve, and retract the lancet back into the sleeve automatically when the pressure on the rod ceases, without deteriorating the other main functions of the device, while at the same time the device provided with tongues can be manufactured in the same advantageous manner as that described in the introduction.

The device according to the invention is characterized in that each tongue is defined by axial slits formed in the wall of the sleeve, that the tongues extend radially obliquely into the sleeve with their free ends located immediately inside the front end or an orifice ring of the sleeve, the distance between the free ends of the tongues when the rod assumes said starting position, being less than the thickness of the rod at the end proviced with the lancet, and that the tongues are arranged to cooperate with the end of the rod provided with the lancet upon movement of the lancet in said directions.

The invention will be described more fully in the following with reference to the accompanying drawings.

FIG. 6 is a side view of a second embodiment of the device according to the invention in a starting position ready for use.

FIG. 7 is a longitudinal section view of the device according to FIG. 6.

FIG. 8 is a longitudinal section view of the device according to FIG. 6 in operative position.

Figure 1:
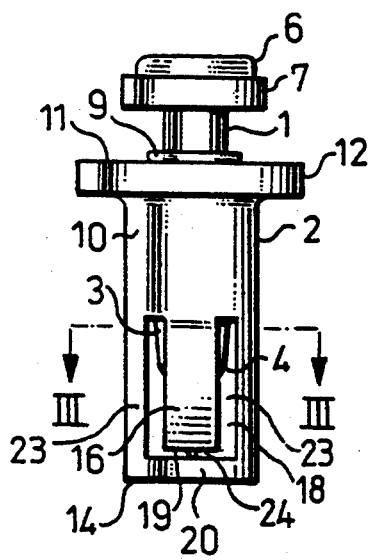
FIG. 1 is a side view of a first embodiment of the device according to the invention in a starting position ready for use.

The device schematically shown in the drawings is of disposable type and consists of two parts in the form of a rod 1 and a sleeve 2 which cooperate with each other.

The rod 1 comprises a solid body 3 with a lancet 5 of suitable metal protruding axially at and from the front end surface 27 of the body, and a circular pressure plate 7 located at the rear end 6 of the body 3. The body 3 and pressure plate 7 of the rod 1 are manufactured in one piece of some suitable plastic material, the lancet 5 being embedded simultaneously in the body during this manufacture so that it is permanently fixed in the solid body 3 and so that a portion with a tip 8 projects axially from the body.

The sleeve 2, acting as carrier and guide means for the rod 1, comprises a generally cylindrical, hollow body 10 and a finger-grip plate 12 located at the rear end 11 of the body 10. The body 10 is provided with an axially cylindrical through-hole 13 to receive the body 3 of the rod 1 without friction, leaving a clearance therebetween.

The rod 1 and sleeve 2 are so adapted with respect to each other that when the rod 1 is fully inserted into the sleeve 2, the tip 8 of the lancet will protrude a predetermined distance, e.g. about 0.5-2 mm, from the sleeve 2. Thus, in the embodiment shown, the pressure plate 7 will in this operative end position be in contact with the finger-grip plate 12 or rear end 11 of the sleeve 2. The sleeve 2 is suitably manufactured of the same plastic material as the rod 1.

Figure 2:
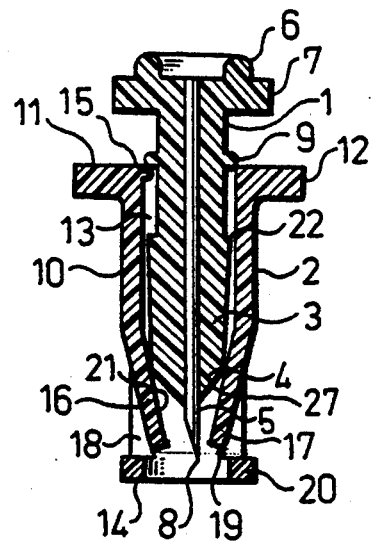
FIG. 2 is a longitudinal section view of the device according to FIG. 1.
Figure 4:
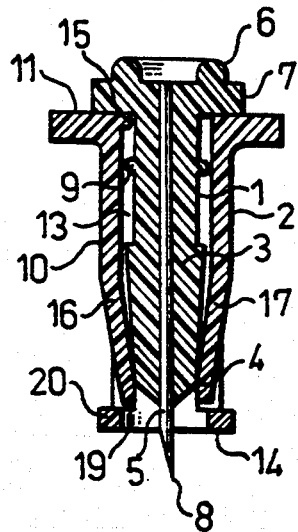
FIG. 4 is a longitudinal section view of the device according to FIG. 1 in operative position.
Figure 5:
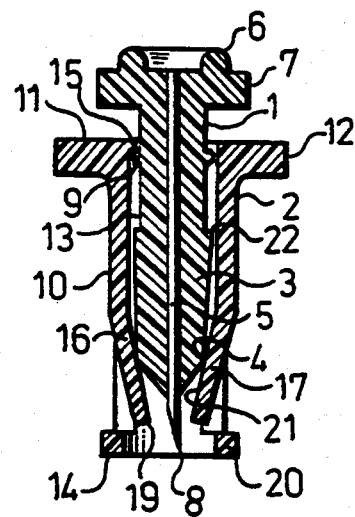
FIG. 5 is a longitudinal section view of the device after use, ready for discarding.

The device further comprises a first stop means functionally adapted to constrict passage or temporarily obstruct movement, said stop means being formed by a first protrusion 9 arranged on the body 3 of the rod 1 at a predetermined distance from the tip 8 of the lancet 5, and a second protrusion 15 arranged on the sleeve 2 at a predetermined distance from the front end 14 thereof to engage with said first protrusion. In the embodiment shown, said protrusion 9 consists of an annular ridge 9, whereas the second protrusion 15 is formed by three warts distributed uniformly around the periphery of the hole wall of the sleeve at the entrance to the hole 13. The protrusion 15 of the sleeve thus forms a constriction of the hole at its entrance, thus preventing continued movement of the rod 1 into the sleeve 2 when its ridge 9 comes into contact with the warts 15 on the sleeve, as illustrated in FIG. 2. By increasing the pressure with the thumb or another finger on the pressure plate 7 of the rod 1, this resistance is finally overcome so that the rod 1 can be inserted the full length determined by the body 3 into the sleeve 2, as illustrated in FIG. 4. When this increased pressure is suddenly released by the protrusions 9, 15 moving past and out of engagement with each other, the rod 1 acquires an extremely high speed into the sleeve 2 the rest of the distance until the second stop means is reached. This second stop means is thus constituted by the pressure plate 7 and the rear end 11 of the sleeve 2. This in turn means that the tip 8 of the lancet is pushed out of the sleeve 2 at a correspondingly high speed, rapidly penetrating the skin and the blood vessels beneath. It will be understood that the front end 14 of the sleeve 2 will be in contact with the skin at least from the point when the pressure is increased on the rod 1 after temporary engagement of the first stop means 9, 15 has been achieved.

The protrusion 9 on the rod 1 is placed at a predetermined point on the body 3 so that the distance between the protrusion 9 and the tip 8 of the lancet will be slightly less than the distance between the front end 14 of the sleeve 2 and the protrusion 15 of the sleeve 2 forming the stop. The lancet 5 acquires a high speed due to the sudden release and insertion of the rod 1 and the tip 8 will therefore penetrate the skin quickly, thus contributing to a relatively low and brief sensation of pain.

Figure 3:
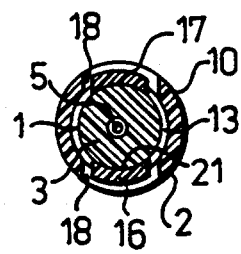
FIG. 3 is a cross section view along the line III—III in FIG. 1.

According to the present invention the sleeve 2 is provided with two diametrically located spring tongues 16, 17 axially aligned and having restricted spring action. Each tongue 16, 17 is formed in one piece with the cylindrical body 10 and is defined laterally by two axial slits 23 and a lower, transverse slit 24, said slits together forming a U-shaped groove 18 as shown in FIG. 1. A short (in axial direction) orifice ring 20 is formed between the front end 14 of the sleeve and the transverse slits 24 of the U-shaped grooves 18, the free ends 19 of the tongues 16, 17 being located immediately inside this orifice ring. The distance therebetween is so short that the lancet 5 is hidden as much as possible but is still sufficient long for the free ends 19 of the tongues to be free of the orifice ring 20 when displaced laterally by the rod 1. The distance is preferably 0.5-1.0 mm. From the root portion, where the tongues 16, 17 are joined to the body 10, the tongues extend radially obliquely into the hole 13 in the cylindrical body so that their mid-sections are in contact with the lower peripheral edge 4 of the body 3 of the rod 1 in an inoperative, starting position when the rod 1 assumes its initial position in relation to the sleeve 2, as illustrated in FIGS. 1 and 2. In this starting position the distance between the two tongues 16, 17, measured between their free ends 19, is less than the thickness of the rod 1 measured at its lower end 4. This difference in distance and thickness is suitably 2-4 mm, preferably 3 mm. The body 3 narrows conically towards the lower peripheral edge 4, thus permitting an inclined starting position of the tongues without their being affected by the rod 1. As evident from FIG. 3 the tongues 16, 17 suitably have a concave inner side 21, seen in cross section, the inner side 21 having a radius substantially corresponding to the radius or circle form of the body 3 at its lower edge or end 4. Thus, as well as guiding the body 3 between them, the tongues 16, 17 also provide guiding action of the body 3 in lateral direction, i.e. the body 3 and lancet 5 are guided in all raidal directions, seen in cross section. When the rod 1 is pushed in, the spring tongues 16, 17 will be bent radially outwards by the body 3. During their spring abutment against the peripheral edge 4 of the body 3 they will guide and centre the body 3 so that this and the lancet 5 acquire a linear movement and so that the central axis of the rod 1 will coincide with the central axis of the sleeve. Centred penetration of the skin is ensured in this way. This in turn contributes to a reduced sensation of pain.

The spring tongues 16, 17 are also sufficiently long to surround the lower peripheral edge 4 of the body 3 even when this is fully pressed into the sleeve 2, so that the free ends 19 of the tongues 16, 17 are located below the lower peripheral edge 4 of the body 3 but spaced slightly therefrom, as illustrated in FIG. 4. When the pressure on the rod 1 is released, thanks to the spring force previously accumulated in them, the tongues 16, 17 will influence the rod 1 to return to a second rear position in which the lancet 5 is fully retracted within the sleeve 2 but not as far as in the temporarily arrested starting position according to FIG. 2. In this way accidental contact with the lancet 5 is prevented, now no longer sterile, and the blood thereon which results in reduced infection risk.

The tongues 16, 17 are shaped and aligned so that their spring force is not so great as to impede the desired quick movement of the rod 1 once the stop 9, 15 have been overcome. On the other hand, the spring force should be sufficient to enable the tongues 16, 17 to press back the rod 1 when the pressure thereon has been released as described above.

The tongues 16, 17 are also sufficiently long to hide the lancet 5 as far as possible from the patient's view, when the lancet 5 assumes its starting position according to FIGS. 1 and 2, and protect the lancet 5 from contamination. The free ends are located immediately inside the orifice ring 20 which in turn prevents the tongues from coming into contact with the skin when the device is pressed against a finger.

The device according to the present invention is advantageously manufactured in one piece, the rod 1 and sleeve 2 being formed as a coherent member or unit which can easily be separated from each other when it is to be used.

The body 3 has a conical portion with a rear edge 22 which provides an additional stop together with the protrusion 15 to prevent the rod 1 from accidentally falling out of the sleeve 2 due to its own weight when the device is turned upside down. When the rod 1 is inserted into the sleeve 2 the edge 22 passes relatively easily over the protrusion 15 since the diameter of the edge is only somewhat larger than the diameter described by a circle coinciding with the protrusion 15 and considerably smaller than the diameter of the ridge 9.

Although two tongues are sufficient to achieve the necessary guidance of the lancet, the sleeve may be provided with more than two tongues, e.g. three or four tongues.

The embodiment shown in FIGS. 6–8 is similar to that described above with the exception of the shapes of the axial slits 23 and the tongues 16, 17. As can be seen more clearly in FIG. 6, the axial slits 23 extend all the way to the front end 14 of the cylinder. Each tongue is bent and comprises an upper portion 25 for spring cooperation with a forward conical end surface 27 of the rod 1 and a lower end portion 26 the purpose of which is to hide the lancet 5 from the patient's view when the lancet 5 assumes its starting position, and to protect the lancet 5 from contamination. The free ends 19 of the end portion 26 shall be located immediately inside the front end 14 of the sleeve 2. The distance between these ends 14, 19 shall be as little as possible in order to achieve optimal protection from view and contamination, but must at the same time be sufficient large for the tongues 16, 17 not to come into contact with the skin when the device is placed on a finger. The important factor is that the tongues 16, 17 are not in contact with the skin thereby retarding insertion of the rod by pressing. To achieve the compromises mentioned above the distance between said ends 14, 19 is suitably from 0.5 mm to 2.0 mm. Allowing the tongues to cooperate with the conical end surface 27 of the rod ensures a particularly efficient return of the tip 8 of the needle into the sleeve 2.

I claim:

1. A disposable device for puncturing human skin and blood vessels beneath to obtain blood for subsequent testing, comprising:

an elongated rod having a first end and a second end, and including an enlarged portion at said first end, and said rod having a largest cross-sectional dimension;

a lancet embedded in said rod extending between the first and second ends thereof and having a tip protruding from said second end of said rod;

an elongated sleeve substantially concentric with said rod and having a through-extending opening, extending from a rear end of said sleeve to a front end of said sleeve, part of said rod disposed within said through-extending opening, but said enlarged portion at said first end of said rod disposed exteriorly of said sleeve, and said rear and front ends of said sleeve spaced from each other a first distance;

a first stop element disposed on said rod between said first and second ends thereof;

a second stop element disposed on said sleeve, cooperating with said first stop element in a first portion;

said first and second stop elements, rod, and sleeve being constructed so that said first stop element may, upon application of sufficient force to said rod enlarged portion at said first end, move past said second stop element;

at least first and second longitudinal spring tongues integral with said sleeve and each having a free end extending into said through-extending opening, said free ends having a spacing less than said rod largest cross-sectional dimension;

said spring tongues engaging said rod adjacent said second end of said rod and providing a spring biasing force centering said rod in said through-extending opening and biasing said rod away from said front end of said sleeve throughout the entire range of movement of said rod until said enlarged portion at said first end of said rod engages and is stopped by said rear end of said sleeve; and said lancet dimensioned so that when said enlarged portion at said first end of said rod engages said sleeve rear end said lancet tip portion protrudes past said front end of said sleeve.

2. A device as recited in claim 1 wherein said spring tongues are constructed to engage said rod, and said first and second stop elements are dimensioned, so that after said lancet tip is moved to a position protruding past said front end of said sleeve by a force applied to said enlarged portion at said rod first end, said spring tongues will automatically move said rod to a position in which said first stop element is within said through-extending opening but engages said second stop element, being stopped thereby in a second position, and said lancet tip portion is within said sleeve.

3. A device as recited in claim 2 wherein said spring tongues are formed by axial slits formed in said sleeve.

4. A device as recited in claim 3 wherein said spring tongue free ends are spaced from each other, when said first and second stop elements are in said first position, about 2–4 mm.

5. A device as recited in claim 3 wherein said spring tongue free ends are spaced from each other, when said first and second stop elements are in said first position, about 3 mm.

6. A device as recited in claim 1 wherein said spring tongues are formed by U-shaped grooves formed in said sleeve.

7. A device as recited in claim 4 wherein said sleeve front end is defined by an orifice ring, and wherein said free ends of said spring tongues are spaced from said orifice ring about 0.5–1.0 mm.

8. A device as recited in claim 1 wherein said free ends of said spring tongues are spaced from said front end of said sleeve about 0.5–2.0 mm when said stop elements are in said first position.

9. A device as recited in claim 1 wherein said rod second end gradually tapers so that it has its smallest cross-section at said lancet adjacent said lancet tip, having a generally conical configuration.

10. A device as recited in claim 1 wherein said second stop element is disposed at said rear end of said sleeve.

11. A device as recited in claim 1 wherein said sleeve is a first integral piece of plastic, and said rod is said second integral piece of plastic, and said lancet is metal.

12. A device as recited in claim 1 wherein said spring tongues consist of two spring tongues spaced approximately 180° from each other.

13. A device as recited in claim 8 wherein said spring tongue free ends are spaced from each other, when said first and second stop elements are in said first position, about 2–4 mm.

14. A device as recited in claim 2 wherein said rod second end gradually tapers so that it has its smallest cross-section at said lancet adjacent said lancet tip, having a generally conical configuration.

15. A device as recited in claim 14 wherein said second stop element is disposed at said rear end of said sleeve.

16. A disposable device for puncturing human skin and blood vessels beneath the skin to obtain blood for subsequent testing, comprising:

a rod having first and second ends, and a lancet concentric with said rod and received by said rod, and having a tip portion extending axially outwardly from said rod second end;

a sleeve receiving said rod, said rod concentric with said sleeve;

first stop means for holding said rod and sleeve with respect to each other in a first position wherein said lancet tip is completely within said sleeve;

second stop means preventing further relative movement between said rod and sleeve once said rod has been moved past said first position to a second position in which said lancet tip extends outwardly from said sleeve;

biasing means for maintaining said lancet concentric with said sleeve and for biasing said rod toward said first position;

third stop means for stopping movement of said rod toward said first position in a third position in which said lancet tip is completely within said sleeve, but closer to extending outwardly from said sleeve than it is in said first position; and wherein said biasing means comprises a plurality of spring tongues integral with said sleeve and bent in toward the center of said sleeve; and wherein said rod comprises a substantially conical portion engaging said spring tongues.

17. A device as recited in claim 16 wherein said plurality of spring tongues consists of two spring tongues spaced approximately 180 degrees from each other.

18. A device as recited in claim 16 wherein said sleeve and said rod are each of plastic; and wherein said first stop means comprises a first surface of a stop element integral with said rod, and a first surface of a stop element integral with said sleeve; and wherein said third stop means comprises a second surface of said stop element integral with said rod, and a second surface of said stop element integral with said sleeve.

* * * * *